(12) United States Patent
Rafii et al.

(10) Patent No.: US 6,852,533 B1
(45) Date of Patent: Feb. 8, 2005

(54) PURIFIED POPULATIONS OF STEM CELLS

(75) Inventors: Shahin Rafii, Great Neck, NY (US); Larry Witte, Stormville, NY (US); Malcolm A. S. Moore, New York, NY (US)

(73) Assignees: Cornell Research Foundation, Inc., Ithaca, NY (US); Sloan-Kettering Institute for Cancer Research, New York, NY (US); ImClone System Incorporated, New York, NY (US)

( * ) Notice: Subject to any disclaimer, the term of this patent is extended or adjusted under 35 U.S.C. 154(b) by 0 days.

(21) Appl. No.: 09/236,729

(22) Filed: Jan. 25, 1999

Related U.S. Application Data

(63) Continuation-in-part of application No. 09/012,903, filed on Jan. 23, 1998.
(60) Provisional application No. 60/072,362, filed on Jan. 23, 1998.

(51) Int. Cl.$^7$ .............................. C12N 5/02; C12N 5/06
(52) U.S. Cl. ..................... 435/372; 435/355; 435/325
(58) Field of Search ................................. 435/325, 355, 435/366, 372; 424/93.1

(56) References Cited

U.S. PATENT DOCUMENTS

| | | | |
|---|---|---|---|
| 5,035,994 A | | 7/1991 | Civin ............................ 435/2 |
| 5,061,620 A | | 10/1991 | Tsukamoto et al. ......... 435/7.21 |
| 5,130,144 A | | 7/1992 | Civin ......................... 424/577 |
| 5,283,354 A | * | 2/1994 | Lemischka ................. 536/23.5 |
| 5,328,695 A | * | 7/1994 | Lucas et al. |
| 5,468,612 A | * | 11/1995 | Cohen et al. |
| 5,599,703 A | * | 2/1997 | Davis et al. |
| 5,672,499 A | * | 9/1997 | Anderson et al. |
| 5,674,722 A | | 10/1997 | Mulligan et al. ......... 435/172.3 |
| 5,733,541 A | * | 3/1998 | Taichman et al. .......... 424/93.1 |
| 5,747,651 A | | 5/1998 | Lemischka ................ 530/387.9 |
| 5,843,633 A | * | 12/1998 | Yin et al. ....................... 435/2 |
| 6,204,011 B1 | * | 3/2001 | Kendall et al. |

FOREIGN PATENT DOCUMENTS

| | | | |
|---|---|---|---|
| WO | WO 94/11499 | * | 5/1994 |
| WO | WO 96/40769 | | 6/1996 |
| WO | WO 98/00523 | | 7/1997 |

OTHER PUBLICATIONS

Peichev et al. Blood 95:952–958, 2000.*
TP Yamaguchi et al., Development, "flk–1, and flt–related receptor tyrosine kinase is an early marker for endothlial cell precursors," 1993, 118, 489–498.*
UM Gehling et al., Blood, "In vitro differentiation of endothelial cells from AC133–positive progenitor cells,"May 2000, vol. 95, No. 10, pp. 3106–3112.*
S. Rafii et al., Blood, "Rapid Communication," Jul. 1994, vol. 84, No. 1, pp. 10–19.*
Almedia–Porada, J. Lab. Clin. Med. 128, 399–407 (1996).*
Vittet et al., Blood 88 3424–3431 (1996).*
Stemple, Cell 71, 973–985 (1992).*
Masek et al., Experimental Hematology 22, 1203–1209 (1994).*
Rohwedel, Development Biology 164, 87–101 (1994).*
Miraglia, et al., A Novel Five–Transmembrane Hematopoietic Stem Cell Antigen: Isolation, Characterization, and Molecular Cloning, Blood 90, 5013–5021 (1997).
Asahara, et al. Isolation of Putative Progenitor Endothelial Cells for Angiogenesis, Science 275, 946–967 (1997).
Eichmann et al., Ligand–Dependent Development of the Endothelial and Hemopoietic Lineages from Embroyonic Mesodermal Cells Expressing Vascular Endothelial Growth Factor Receptor 2, Proc. Natl. Acad. Sci. USA 94, 5141–5146 (1997).
New York Times, Brain Stem Cell Is Discovered Twice, Jun. 16, 1999.
Shalaby, et al., A Requirement for Flkl in Primitive and Definitive Hematopoiesis and Vasculogenesis, Cell 39, 981–990 (1997).
Pepper, Michael, S., Manipulating Angiogenesis Arteriosclerosis, Thrombosis, and Vascular Biology 17, 605–619(1997).
Yin, et al., AC133, A Novel Marker for human Hematopoietic Stem and Progenitor Cells, Blood 90, 5002–5012(1997).

* cited by examiner

Primary Examiner—Ram R. Shukla
(74) Attorney, Agent, or Firm—Kenyon & Kenyon

(57) ABSTRACT

The invention is directed to a purified population of mammalian endothelial, muscle, or neural stem cells. The invention further provides methods for isolating such populations of cells; methods for using such populations of cells for treating mammals; methods for making vectors for gene therapy; and methods for carrying out gene therapy with such vectors.

13 Claims, No Drawings

PURIFIED POPULATIONS OF STEM CELLS

This application is a continuation-in-part of Ser. No. 09/012,903 and claims benefit of provisional application 60/072,362, both of which were filed Jan. 23, 1998, were pending when the present application was filed, and are incorporated herein by reference.

The invention is directed to purified populations of endothelial, muscle and neural progenitor cells and their uses in therapy and in gene therapy.

BACKGROUND OF THE INVENTION

In mammalian embryos, hemangioblasts are believed to be the precursors of angioblasts and totipotent or pluripotent hematopoietic progenitor (i.e. stem) cells. Angioblasts and other embryonic totipotent and/or pluripotent progenitor cells are believed to be the precursors of postnatal endothelial cells, muscle cells, and neural cells. Despite considerable progress, uncertainties regarding these systems remain.

In the hematopoietic system, pluripotent stem cells are believed to be able to repopulate all of the blood cell lineages in an ablated mammal. Various surface markers may be used to obtain purified populations of such stem cells.

For example, a purified population of CD34+ hematopoietic stem cells was described by Civin in U.S. Pat. Nos. 5,035,994 and 5,130,144. A more highly purified population of hematopoietic stem cells that are CD34+, Class II HLA+, and Thy-1+ was described by Tsukamoto et al. in U.S. Pat. No. 5,061,620.

The Tsukamoto patent further explains that stem cells lack certain markers that are characteristic of more mature, lineage-committed (Lin+) cells. Such markers include CD3, CD8, CD10, CD19, CD20, and CD33. Cells that lack these markers are said to be lineage negative (Lin−).

The development of the initial blood vessel system in embryos is generally believed to occur from the adhesion to each other and modeling of primitive endothelial precursor cells, such as angioblasts. This process is known as vasculogenesis.

Postnatal development of new blood vessels is generally believed to occur from the proliferation, migration, and remodeling of the mature endothelial cells of pre-existing blood vessels. This process is known as angiogenesis.

It has been suggested that angioblasts and hematopoietic stem cells share certain surface markers, such as CD34 and the FLK-1 receptor. The FLK-1 receptor is also known as vascular endothelial growth factor receptor-2 (VEGFR-2) and, in the case of the human receptor, KDR. These suggestions have led to speculation that CD34+ mononuclear blood cells isolated from human peripheral blood may contribute to neoangiogenesis. See, for example, Pepper, Arteriosclerosis, Thrombosis, and Vascular Biology 17, 605–619 (April, 1997); Asahara et al., Science 275, 964–967 (Feb. 14, 1997).

There have been no reports that establish with confidence the existence of a population of endothelial, muscle, or neural progenitor cells comparable to hematopoietic progenitor cells, or, a fortiori, a method of isolating and purifying such cells.

Little is known with confidence, moreover, about the surface markers that differentiate endothelial progenitor cells from mature cells. For example, although CD34 appears to be a surface marker on endothelial progenitor cells, some mature endothelial cells also are CD34+.

The lack of information regarding surface markers on endothelial, muscle, or neural progenitor cells has made it difficult to isolate purified populations of these cells that can be used for therapeutic purposes. Such populations of progenitor cells are believed to be recruited at sites of cell growth and organ formation, at least in embryos. Less is known about the development of new cells and organs in adults.

The object of the present invention is to provide purified populations of endothelial, muscle, and neural stem cells. Another object of the present invention is to provide methods for isolating such stem cells. Another object of the present invention is to provide methods whereby populations of endothelial, muscle, and neural stem cells can be used in the treatment of conditions that require neovascularization, neomyogenesis, and neoneurogenesis, as well as in gene therapy.

SUMMARY OF THE INVENTION

These objectives, and other objectives as will be apparent to those having ordinary skill in the art, have been met by providing a purified population of mammalian endothelial stem cells, muscle stem cells and neural stem cells. The invention further provides methods for isolating such populations of stem cells; methods for using such populations of stem cells for treating mammals in need of neovascularization, neomyogenesis, and neoneurogenesis; methods for making vectors for gene therapy; and methods for carrying out gene therapy with such vectors.

DETAILED DESCRIPTION OF THE INVENTION

Definitions

The invention is directed to purified populations of mammalian stem cells. For the purpose of describing the invention in this specification, a stem cell is any immature cell that can develop into a more mature cell.

The stem cells may be endothelial stem cells, muscle stem cells, or neural stem cells. An endothelial stem cell is a stem cell that is capable of maturing at least into a more mature endothelial cells. A muscle stem cell is a stem cell that is capable of maturing at least into a more mature muscle cells. A neural stem cell is a stem cell that is capable of maturing at least into a more mature neural cells.

The muscle cells can be, for example, skeletal muscle cells, smooth muscle cells, and cardiac muscle cells. Smooth muscle cells include, for example, the muscle cells of blood vessels and of the gastrointestinal tract.

The stem cells may be pluripotent, bipotent, or monopotent. Monopotent stem cells are also referred to as progenitor cells. Pluripotent stem cells, bipotent stem cells, and progenitor cells are capable of developing into mature cells either directly, or indirectly through one or more intermediate stem or progenitor cells.

Pluripotent endothelial stem cells are capable of developing into more than two types of mature endothelial cells or into mature endothelial cells and at least two other types of mature cells, such as, for example, neural cells and muscle cells. Bipotent endothelial stem cells are capable of developing into mature endothelial cells and one other type of mature cell, such as, for example, neural cells or muscle cells. Progenitor endothelial cells are capable of developing only into mature endothelial cells.

Pluripotent muscle stem cells are capable of developing into more than two types of mature muscle cells or into mature muscle cells and at least two other types of mature cells, such as, for example, neural cells and endothelial cells.

Bipotent muscle stem cells are capable of developing into mature muscle cells and one other type of mature cell, such as, for example, neural cells or endothelial cells. Progenitor muscle cells are capable of developing only into mature muscle cells.

Pluripotent neural stem cells are capable of developing into more than two types of mature neural cells or into mature neural cells and at least two other types of mature cells, such as, for example, endothelial cells and muscle cells. Bipotent neural stem cells are capable of developing into mature neural cells and one other type of mature cell, such as, for example, endothelial cells or muscle cells. Progenitor neural cells are capable of developing only into mature neural cells.

According to the above definitions, the term pluripotent stem cell always includes bipotent stem cells and progenitor cells. The term bipotent stem cell always includes progenitor cells. For example, stem cells include, but are not limited to, angioblasts.

The word mammal means any mammal. Some examples of mammals include pet animals, such as dogs and cats; farm animals, such as pigs, cattle, sheep, and goats; laboratory animals, such as mice and rats; primates, such as monkeys, apes, and chimpanzees; and humans.

The stem cells of the invention are characterized by highly expressed surface antigens. Such antigens include, for example, one or more vascular endothelial growth factor receptor (VEGFR). Examples of VEGFRs include FLK-1 and FLT-1. The FLK-1 receptor is also known by other names, such as VEGFR-2. Human FLK-1 is sometimes referred to in the literature and herein as KDR.

At least some of the stem cells also express the CD34+ marker. The stem cells may be further characterized by the absence or significantly lower expression levels of certain markers characteristic of mature cells. Such markers include CD1, CD2, CD3, CD4, CD5, CD8, CD10, CD11b, CD13, CD14, CD 15, CD16, CD19, CD20, CD24, CD25, CD28, CD29, CD33, CD36, CD38, CD41, CD41a, CD56, CD66b, CD66e CD69, and glycophorin A. Cells lacking some or all of these markers will be referred to as Lin−.

In addition, at least some stem cells also express the AC133 antigen, which was described by Yin et al. in Blood 90, 5002–5112 (1997) and by Miraglia et al. in Blood 90, 5013–5021 (1997). The AC 133 antigen is expressed on stem cells, but not on mature cells.

Most, if not all, of the stem cells express FLK-1. The CD34 marker is also characteristic of stem cells, such as angioblasts and hematopoietic stem cells. Approximately 0.5–10% of CD34+ cells are also FLK-1+. For example, approximately 1% of bone marrow cells are CD34+. Of the CD34+ marrow cells, approximately 1% are FLK-1+.

Populations of Endothelial Stem Cells

In one embodiment, the invention relates to a method of isolating populations of endothelial, muscle, or neural stem cells. The population of cells may be isolated by means of positive selection, or by a mixture of both positive and negative selection in either order.

The population of stem cells is purified. A purified population of stem cells contains a significantly higher proportion of stem cells than the crude population of cells from which the stem cells are isolated.

For example, the purification procedure should lead at least to a five fold increase, preferably at least a ten fold increase, more preferably at least a fifteen fold increase, most preferably at least a twenty fold increase, and optimally at least a twenty-five fold increase in stem cells with respect to the total population. The purified population of stem cells should include at least 15%, preferably at least 20%, more preferably at least 25%, most preferably at least 35%, and optimally at least 50% of stem cells.

The methods described in this specification can lead to mixtures comprising up to 75%, preferably up to 80%, more preferably up to 85%, most preferably up to 90% and optimally up to 95% of stem cells. Such methods are capable of producing mixtures comprising 99%, 99.90% and even 100% of stem tells. Accordingly, the purified populations of the invention contain significantly higher levels of stem cells than those that exist in nature, as described above.

The purified population of stem cells may be isolated by contacting a crude mixture of cells containing a population of stem cells that express an antigen characteristic of stem cells with a molecule that binds specifically to the extracellular portion of the antigen. Such a technique is known as positive selection.

The binding of the stem cells to the molecule permit the stem cells to be sufficiently distinguished from contaminating cells that do not express the antigen to permit isolating the stem cells from the contaminating cells. The antigen is preferably VEGFR, and more preferably FLK-1.

The molecule used to separate stem cells from the contaminating cells can be any molecule that binds specifically to the antigen that characterizes the stem cell. The molecule can be, for example, a monoclonal antibody, a fragment of a monoclonal antibody, or, in the case of an antigen that is a receptor, the ligand of that receptor. For example, in the case of a VEGF receptor, such as FLK-1, the ligand is VEGF.

The number of antigens, such as VEGF receptors, characteristic of stem cells found on the surface of such cells, must be sufficient to isolate purified populations of such cells. For example, the number of antigens found on the surface of stem cells should be at least approximately 1,000, preferably at least approximately 5,000, more preferably at least approximately 10,000, most preferably at least approximately 25,000, and optimally at least approximately 100,000. There is no limit as to the number of antigens contained on the surface of the cells. For example, the cells may contain approximately 150,000, 250, 000, 500,000, 1,000,000, or even more antigens on the surface.

The source of cells from which purified endothelial, muscle, and neural stem cells are derived may be any natural or non-natural mixture of cells that contains stem cells. The source may be derived from an embryonic mammal, or from the post-natal mammal.

One source of cells is the hematopoietic microenvironment, such as the circulating peripheral blood, preferably from the mononuclear fraction of peripheral blood, umbilical cord blood, bone marrow, fetal liver, or yolk sac of a mammal. The stem cells, especially neural stem cells, may also be derived from the central nervous system, including the meninges.

Either before or after the crude cell populations are purified as described above, the population of stem cells may be further concentrated by methods known in the art. For example, the stem cells can be enriched by positive selection for one or more antigens characteristic of stem cells. Such antigens include, for example, FLK-1, CD34, and AC133.

For example, human stem cells may be pre-purified or post-purified by means of an anti-CD34 antibody, such as the anti-My-10 monoclonal antibody described by Civin in U.S. Pat. No. 5,130,144. The hybridoma cell line that expresses the anti-My monoclonal antibody is available from the American Type Culture Collection, 12301 Parklawn Drive, Rockville, Md. 20852, USA. Some additional sources of antibodies capable of selecting CD34+ cells include AMAC, Westbrook, Me.; Coulter, Hialea, Fla.; and Becton Dickinson, Mountain View, Calif. CD34+ cells may also be isolated by means of comparable antibodies, which may be produced by methods known in the art, such as those described by Civin in U.S. Pat. No. 5,130,144.

In addition, or as an alternative to, the enrichment with anti-CD34 antibodies, populations of stem cells may also be further enriched with the AC 133 antibodies described by Yin et al. in Blood 90, 5002–5112 (1997) and by Miraglia et al. in Blood 90, 50135021 (1997). The AC133 antibodies may be prepared in accordance with Yin et al.; ibid, or purchased from Miltenyi Biotec.

The preferred cells of the invention are either FLK-1+ CD34+ AC 133+; FLK-1+CD34−AC133+; FLK-1+CD34+ AC133−; or FLK-1+CD34−AC1336−.

Cells may be further enriched for stem cells by removing cells that are lin+. Such a method is known as negative selection. Negative selection may be used either before or after positive selection.

Thus, molecules, such as antibodies or fragments of antibodies, that bind to all or any combination of CD1, CD2, CD3, CD4, CD5, CD8, CD10, CD11b, CD13, CD14, CD15, CD16, CD19, CD20, CD24, CD25, CD28, CD29, CD33, CD36, CD38, CD41, CD41a, CD56, CD66b, CD66e, CD69, and glycophorin A may be used to remove the unwanted Lin+ cells by the same methods described above for positive selection.

The stem cells isolated and purified as described herein are primary cells. The primary cells may be cultured and passaged. Being passaged refers to the dividing of a cell population into portions in order to allow further expansion of the cell population. The stem cells administered therapeutically to mammals, as described below, may be cells that have been passaged, but are preferably primary cells. The primary cells may be cultured, but they are preferably not passaged.

Techniques of Isolating Stem Cells

A mixture of cells from a suitable source of endothelial, muscle, and/or neural stem cells, as described above, is harvested from a mammalian donor by methods known in the art. A suitable source is the hematopoietic microenvironment.

For example, circulating peripheral blood, preferably mobilized (i.e., recruited) as described below, may be removed from a patient. Alternatively, bone marrow may be obtained from a mammal, such as a human patient, undergoing an autologous transplant.

The mixture of cells obtained are exposed to a molecule that binds specifically to the antigen marker characteristic of stem cells. The binding molecule is preferably an antibody or a fragment of an antibody. A convenient antigen marker is a VEGF receptor, more specifically a FLK-1 receptor.

The cells that express the antigen marker bind to the binding molecule. The binding molecule distinguishes the bound cells from unbound cells, permitting separation and isolation. If the bound cells do not internalize the molecule, the molecule may be separated from the cell by methods known in the art. For example, antibodies may be separated from cells by a short exposue to a solution having a low pH, or with a protease such as chymotrypsin.

The molecule used for isolating the purified populations of stem cells is advantageously conjugated with labels that expedite identification and separation. Examples of such labels include magnetic beads; biotin, which may be identified or separated by means of its affinity to avidin or streptavidin; fluorochromes, which may be identified or separated by means of a fluorescence-activated cell sorter (FACS, see below), and the like.

Any technique may be used for isolation as long as the technique does not unduly harm the stem cells. Many such methods are known in the art.

In one embodiment, the binding molecule is attached to a solid support. Some suitable solid supports include nitrocellulose, agarose beads, polystyrene beads, hollow fiber membranes, magnetic beads, and plastic petri dishes.

For example, the binding molecule can be covalently linked to Pharmacia Sepharose 6 MB macro beads. The exact conditions and duration of incubation for the solid phase-linked binding molecules with the crude cell mixture will depend upon several factors specific to the system employed, as is well known in the art.

Cells that are bound to the binding molecule are removed from the cell suspension by physically separating the solid support from the remaining cell suspension. For example, the unbound cells may be eluted or washed away with physiologic buffer after allowing sufficient time for the solid support to bind the stem cells.

The bound cells are separated from the solid phase by any appropriate method, depending mainly upon the nature of the solid phase and the binding molecule. For example, bound cells can be eluted from a plastic petri dish by vigorous agitation. Alternatively, bound cells can be eluted by enzymatically "nicking" or digesting an enzyme-sensitive "spacer" sequence between the solid phase and an antibody. Suitable spacer sequences bound to agarose beads are commercially available from, for example, Pharmacia.

The eluted, enriched fraction of cells may then be washed with a buffer by centrifugation and preserved in a viable state at low temperatures for later use according to conventional technology. The cells may also be used immediately, for example by being infused intravenously into a recipient.

In a particularly preferred variation of the method described above, blood is withdrawn directly from the circulating peripheral blood of a donor. The blood is percolated continuously through a column containing the solid phase-linked binding molecule, such as an antibody to Flk-1, to capture stem cells. The stem cell-depleted blood is returned immediately to the donor's circulatory system by methods known in the art, such as hemapheresis. The blood is processed in this way until a sufficient number of stem cells binds to the column. The stem cells are then isolated from the column by methods known in the art. This method allows rare peripheral blood stem) cells to be harvested from a very large volume of blood, sparing the donor the expense and pain of harvesting bone marrow and the associated risks of anesthesia, analgesia, blood transfusion, and infection. Other methods for isolating the purified populations of stem cells are also known. Such methods include magnetic separation with antibody-coated magnetic beads, and "panning" with an antibody attached to a solid matrix.

Methods for removing unwanted cells by negative selection are also known. For example, unwanted cells in a starting cell population are labeled by an antibody, or by a cocktail of antibodies, to a cell surface protein characteristic of Lin+ cells. The unwanted antibody-labeled cells are removed by methods known in the art. For example, the labeled cells can be immobilized on a column that binds to the antibodies and captures the cells.

Alternatively, the antibody that binds the cell surface proteins can be linked to magnetic colloids for capture of unwanted cells on a column surrounded by a magnetic field. This system is currently available through StemCell Technologies Inc., Vancouver, British Columbia, Canada. The remaining cells that flow through the column for collection are enriched in cells that do not express the cell surface proteins that the tetrameric antibodies were directed against. The antibody cocktail that can be used to deplete unwanted Lin+ cells can be custom made to include antibodies against lineage specific markers, such as, for example, CD2, CD3, CD4, CD5, CD8, CD10, CD11b, CD13, CD14, CD15, CD16, CD19, CD20, CD24, CD25, CD28, CD29, CD33, CD36, CD38, CD41, CD56, CD66b, CD66e, CD69, and glycophorin A. The desired cells that lack these markers are not lineage commited, i.e. Lin–.

General Fluorescence Activated Cell Sorting (FACS) Protocol

In a preferred embodiment, a labeled binding molecule is bound to the stem cells, and the labeled cells are separated by a mechanical cell sorter that detects the presence of the label. The preferred mechanical cell sorter is a fluorescence activated cell sorter (FACS). FACS machines are commercially available. Generally, the following FACS protocol is suitable for this procedure:

A Coulter Epics Eliter sorter is sterilized by running 70% ethanol through the systems. The lines are flushed with sterile distilled water.

Cells are incubated with a primary antibody diluted in Hank's balanced salt solution supplemented with 1% bovine serum albumin (HB) for 60 minutes on ice. The cells are washed with HB and incubated with a secondary antibody labeled with fluorescein isothiocyanate (FITC) for 30 minutes on ice. The secondary label binds to the primary antibody. The sorting parameters, such as baseline fluorescence, are determined with an irrelevant primary antibody. The final cell concentration is usually set at one million cells per ml.

While the cells are being labeled, a sort matrix is determined using fluorescent beads as a means of aligning the instrument.

Once the appropriate parameters are determined, the cells are sorted and collected in sterile tubes containing medium supplemented with fetal bovine serum and antibiotics, usually penicillin, streptomycin and/or gentamicin. After sorting, the cells are re-analyzed on the FACS to determine the purity of the sort.

Methods for Inducing Neovascularization, Neomyogenesis and Neoneurogenesis with Endothelial, Muscle, and Neural Stem Cells The invention is further directed to a method for inducing neovascularization, neomyogenesis, and neoneurogenesis in a mammal. The method comprises treating the mammal with an effective amount of a purified population of endothelial, muscle, or neural stem cells. Any one of the three types of stem cells may be used to induce any one of the three types of new mature cells, e.g., neovascularization, neomyogenesis, and neoneurogenesis In this specification, neovascularization refers to the development of new blood vessels in a postnatal mammal from endothelial, muscle, or neural stem cells by any means, such as by vasculogenesis followed by linking of the new blood vessels to existing blood vessels, angiogenesis, or the formation of new blood vessels that form as a result of the ability of endothelial stem cells to bind to existing blood vessels and to grow into new blood vessels.

Similarly, neomyogenesis refers to the development of new muscle cells and tissue in a postnatal mammal from endothelial, muscle, or neural stem cells by any mechanism. Neoneurogenesis refers to the development of new neural cells and tissue in a postnatal mammal from endothelial, muscle, or neural stem cells by any mechanism.

There are numerous conditions that cause the necessity of a mammal to be in need of neovascularization. For example, the mammal may have a wound that requires healing. The wound may be an acute wound, such as those caused by burns and contact with hard and/or sharp objects. For example, patients recovering from surgery, such as cardiovascular surgery, cardiovascular angioplasty, carotid angioplasty, and coronary angioplasty all require neovascularization.

The wound may also be a chronic wound. Some examples of chronic wounds include ulcers, such as vascular ulcers and diabetic ulcers.

Inducing neovascularization from stem cells is especially effective in increasing cardiac or peripheral (i.e. limb) vascularization. Therefore, the method is especially effective in treating cardiac and peripheral ischemia.

Patients suffering from other conditions also require neovascularization. Such conditions include sickle cell anemia and thalassemia.

Mammals in need of neomyogenesis include mammals that suffer from injury to the central nervous system, especially the spinal cord; Parkinson's disease; and Alzheimer's disease. Mammals in need of neoneurogenesis include mammals that suffer from injury to the cardiac or skeletal muscle system, and mammals that suffer from muscular dystrophy.

The purified population of endothelial, muscle, or neural stem cells are introduced into a mammal in any way that will cause the cells to migrate to the site where the stem cells are needed. For example, the stem cells may be introduced into a mammal intravenously, by means of a catheter, or directly into the site by, for example, injection.

The endothelial, muscle, or neural stem cells that are administered to a mammal for inducing neovascularization, neomyogenesis, or neoneurogenesis may be autologous or heterologous. Preferably, the stem cells are autologous to the recipient mammal. For example, the cells may be administered after surgery, preferably approximately 0.1–24 hours after surgery.

The stem cells may be recruited into the site that requires new cells and tissues. For example, stem cells may be mobilized (i.e., recruited) into the circulating peripheral blood by means of cytokines, such as, for example, G-CSF, GM-CSF, VEGF, SCF (c-kit ligand) and bFGF, chemokines, such as SDF-1, or interleukins, such as interleukins 1 and 8. Stem cells may also be recruited to the circulating peripheral blood of a mammal if the mammal sustains, or is caused to sustain, an injury.

Vector for Gene Therapy

In another embodiment, the invention is directed to a method for producing a vector useful in gene therapy. The method comprises introducing a gene into a stem cell of the invention. The gene is introduced into the stem cell under the control of suitable regulatory sequences so that the stem cells express the protein encoded by the gene.

Some examples of genes useful for introduction into endothelial, muscle, or neural stem cells include those that encode Factor VIII, von Willebrand factor, insulin, tissue plasminogen activator, any of the interleukins, or a growth factor. Some examples of interleukins include IL-1, -2, -3, -4, -5, -6, -7, -8, -9, -10, -11, -12, -13, -14, -15, -16, -17, -18, -19, -20, and -21. Some examples of suitable growth factors include erythropoietin, thrombopoietin, PDGF, G-CSF, GM-CSF, IGF, TGFβ, VEGF, BMP (bone morphogenic protein) and CNTF (ciliary neurotrophic factor).

Genes may be introduced into stem cells by methods known in the art. For example, genes may be introduced into endothelial stem cells, as well as into muscle and neural cells, by methods described, for example, in Mulligan, et al., U.S. Pat. No. 5,674,722. The methods described in Mulligan, et al., U.S. Pat. No. 5,674,722 for preparing vectors useful for introducing genes into cells, and for introducing genes into endothelial cells, are incorporated herein by reference.

Briefly, the gene to be introduced into cells is placed under the control of one or more inducible or uninducible regulatory sequences in a standard expression vector and transfected directly into a stem cell by known methods, including, for example, standard lipid-mediated, calcium phosphate, or electroporation techniques.

Alternatively, the gene can be cloned into vectors derived from viruses such as adenovirus, adeno-associated virus, herpesvirus, retrovirus or lentivirus. Gene expression is controlled by inducible or uninducible regulatory sequences.

By virtue of a selectable marker present in the aforementioned vectors, such as a neomycin or puromycin resistance gene or the genes for green or blue fluorescence proteins (GFP or BFP), cells infected or transfected as described above are screened, isolated and propogated to obtain a stock of virus, or cells harboring the virus, expressing the gene of interest. Stem cells may be isolated as described herein and exposed to viral vectors (i.e. infected) in serum-containing or serum-free ex vivo no culture conditions for hours or days in the presence of growth factors such as SCF, Flt-3 ligand, TPO, IL-1,3, 6, 11, G-CSF, anti-TGFβ antibodies, and mesodermal factors, to support survival and proliferation of the stem cells.

Infected cells can also be isolated by standard drug selection procedures for neomycin and puromycin or by flow cytometric cell sorting for GFP or BFP expressing cells. The transduced cells may be returned back to the patient as described herein, i.e. intravenous injection, intra-tissue injection, or by means of a catheter.

Gene Therapy

The invention also includes methods for introducing genes to a mammal at a site to which the stem cells of the invention can be recruited. For example, purified populations of endothelial stem cells can be recruited to sites of angiogenesis. Purified populations of muscle stem cells can be recruited to muscles, especially to the musculature of the cardiovascular system, for example, to the heart and blood vessels. Purified populations of neural stem cells can be recruited to the peripheral and central nervous systems, i.e. to the brain and spinal column.

In one embodiment, the method comprises treating the mammal with endothelial, muscle, or neural stem cells, into which a gene under the control of suitable regulatory sequences has been introduced so that the stem cells express the protein encoded by the gene. Examples of suitable genes are those mentioned in connection with the vectors for gene therapy described above. The genes and vectors can be administered to mammals by known methods, including the methods described above.

Selection of the genes to be introduced into stem cells will depend on the application of the gene therapy. For example, gene therapy with endothelial stem cells may be used to promote angiogenesis, inhibit angiogenesis, or to inhibit the growth of tumors.

Some examples of genes useful for promoting angiogenesis include the genes that encode the VEGFs, the cadherins, the integrins, FGFα, FGFβ, FGF4, HGF, TGFα, EGF, angiopoietin-1, B61, IL-8, and angiogenin.

Some examples of genes useful for inhibiting angiogenesis include the genes that encode soluble KDR, soluble flt-1, KDR antibodies, TGF-β, lymphotoxin, interferon-γ, platelet factor 4, angiopoietin-2, angiostatin, endostatin, thrombospondin, inducible protein-10, and IL-12.

Some examples of genes useful for inhibiting tumors include the genes that encode antibodies to EGF receptor, TPA, and urokinase. Some examples of genes useful for treating genetic diseases, for example hemophilia or diabetes, include the genes that encode factor VIII/von Willebrand, factor IX, and insulin.

The gene is delivered at a desired site of neovascularization. The site of neovascularization may be a natural site or an artificially created site. Natural sites of neovascularization include cardiac and peripheral ischemia, tumors, vascular ulcers and other vascular wounds as described above.

The endothelial stem cells transfected with a gene therapy vector may be naturally or artificially recruited to the site where the protein expressed by the gene is desired. Recruiting the vector to the site can be induced artificially by administering a suitable chemokine systemically or at the desired site. A suitable chemokine is stromal derived factor-1 (SDF-1). The endothelial stem cells may also be recruited to the desired site by means of an interleukin, such as IL-1 or IL-8.

The transfected endothelial stem cells that are administered to a mammal for gene therapy may be autologous or heterologous. Preferably, the transfected stem cells are autologous.

Other methods for carrying out gene therapy in mammals have been described in the prior art, for example, in Mulligan, et al., U.S. Pat. No. 5,674,722. The methods described in Mulligan, et al., U.S. Pat. No. 5,674,722 for carrying out gene therapy are incorporated herein by reference.

Isolating Receptors

Receptors and markers that can serve as antigens for making monoclonal antibodies are known in the art. For example, the FLK-1 receptor and gene can be isolated by methods described by Lemischka, U.S. Pat. No. 5,283,354; Matthews, et al., Proc. Natl. Acad. Sci. U.S.A. 88, 9026 (1991); Terman, et al., WO92/14748 and Terman, et al., Biochem. Biophys. Res. Commun. 187, 1579 (1992). The AC 133 antigen can be prepared as described by Yin et al. in Blood 90, 5002–5112 (1997).

Preparation of Receptors

In order to prepare the antigens against which the antibodies are made, nucleic acid molecules that encode the antigen, such as a VEGF receptor or AC 133 antigen, especially the extracellular portions thereof, may be inserted into known vectors for expression using standard recombinant DNA techniques. Standard recombinant DNA techniques are described in Sambrook et al., "Molecular Cloning," Second Edition, Cold Spring Harbor Laboratory Press (11987) and by Ausubel et al. (Eds) "Current Protocols in Molecular Biology," Green Publishing Associates/Wiley-Interscience, New York (1990). The vectors may be circular (i.e. plasmids) or non-circular. Standard vectors are available for cloning and expression in a host.

The host may be prokaryotic or eukaryotic. Prokaryotic hosts are preferably *E. coli*. Preferred eucaryotic hosts include yeast, insect and mammalian cells. Preferred mammalian cells include, for example, CHO, COS and human cells.

The DNA inserted into a host may encode the entire extracellular portion, or a soluble fragment thereof. The extracellular portion of the receptor encoded by the DNA is optionally attached at either, or both, the 5' end or the 3' end to additional amino acid sequences.

The additional amino acid sequence may be attached to the extracellular region in nature, such as those that represent the leader sequence, the transmembrane region and/or the intracellular region of the antigen.

The additional amino acid sequences may also be sequences not attached to the receptor in nature. Preferably, such additional amino acid sequences serve a particular purpose, such as to improve expression levels, solubility, purification, ability to assay, or immunogeneity. Some suitable additional amino acid sequences include, for example, (a) the FLAG peptide optionally attached at either end of the receptor; (b) the Fc portion of an immunoglobulin (Ig), preferably attached at the C-terminus of the receptor; or (c) the enzyme human placental alkaline phosphatase (AP), (Flanagan and Leder, Cell 53, 185–194 (1990)).

Source of DNA Encoding Receptors

In order to produce nucleic acid molecules encoding the receptor, a source of cells that express the receptor is provided. Suitable fetal (i.e. pre-natal) sources include liver, spleen, kidney, or thymus cells. Suitable post-natal sources include bone marrow, umbilical cord endothelial cells or blood, such as circulating peripheral blood, or umbilical cord blood, etc.

Isolation of Nucleic Acid Molecules Encoding Receptors

Total RNA is prepared by standard procedures from receptor-containing tissue or cells. The total RNA is used to direct cDNA synthesis. Standard methods for isolating RNA and synthesizing cDNA are provided in standard manuals of molecular biology such as, for example, in Sambrook et al., "Molecular Cloning," Second Edition, Cold Spring Harbor Laboratory Press (1987) and in Ausubel et al., (Eds), "Current Protocols in Molecular Biology," Greene Associates/Wiley Interscience, New York (1990).

The cDNA of the receptors may be amplified by known methods. For example, the cDNA may be used as a template for amplification by polymerase chain reaction (PCR); see Saiki et al., Science, 222, 487 (1988) or Mullis et al., U.S. Pat. No. 4,683,195. The sequences of the oligonucleotide primers for the PCR amplification are derived from the sequences of the desired receptor.

The oligonucleotides may be synthesized by methods known in the art. Suitable methods include those described by Caruthers in Science 230, 281–285 (1985).

In order to isolate the entire protein-coding regions for the receptors, the upstream PCR oligonucleotide primer is complementary to the sequence at the 5' end, preferably encompassing the ATG start codon and at least 5–10 nucleotides upstream of the start codon. The downstream PCR oligonucleotide primer is complementary to the sequence at the 3' end of the desired DNA sequence. The desired DNA sequence preferably encodes the entire extracellular portion of the receptor, and optionally encodes all or part of the transmembrane region, and/or all or part of the intracellular region, including the stop codon. A mixture of upstream and downstream oligonucleotides are used in the PCR amplification. The conditions are optimized for each particular primer pair according to standard procedures. The PCR product may be analyzed by methods known in the art for cDNA having the correct size, corresponding to the sequence between the primers. Suitable methods include, for example, electrophoresis.

Alternatively, the coding region may be amplified in two or more overlapping fragments. The overlapping fragments are designed to include a restriction site permitting the assembly of the intact cDNA from the fragments.

The DNA encoding the flk-1 receptors may also be replicated in a wide variety of cloning vectors in a wide variety of host cells. The host cell may be prokaryotic or eucaryotic.

The vector into which the DNA is spliced may comprise segments of chromosomal, non-chromosomal and synthetic DNA sequences. Some suitable prokaryotic cloning vectors include plasmids from *E. coli*, such as colE1, pCRM, pBR322, pMB9, pUC, pKSM, and RP4. Prokaryotic vectors also include derivatives of phage DNA such as M13 and other filamentous single-stranded DNA phages.

Expression and Isolation of Receptors

DNA encoding the receptors are inserted into a suitable expression vector and expressed in a suitable prokaryotic or eucaryotic host. Vectors for expressing proteins in bacteria, especially *E. coli*, are known. Such vectors include the PATH vectors described by Dieckmann and Tzagoloff in J. Biol. Chem. 260, 1513–1520(1985). These vectors contain DNA sequences that encode anthranilate synthetase (TrpE) followed by a polylinker at the carboxy terminus. Other expression vector systems are based on beta-galactosidase (pEX); lambda $P_L$; maltose binding protein (pMAL); and glutathione S-transferase (pGST)—see Gene 67, 31 (1988) and Peptide Research 3, 167 (1990).

Vectors useful in yeast are available. A suitable example is the $2\mu$ plasmid.

Suitable vectors for use in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

Further eukaryotic expression vectors are known in the art, e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601–621 (1982); R. J: Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654–4659 (1983); G Urlaub and L. A. Chasin, Proc. Natl. Acad. Sci. USA 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the =system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Vectors containing the receptor-encoding DNA and control signals are inserted into a host cell for expression of the receptor. Some useful expression host cells include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRCI, *Pseudomonas, Bacillus*, such as *Bacillus subtilis*, and *Streptomyces*. Suitable eukaryotic cells include yeast and fungi, insect, animal cells, such as COS cells and CHO cells, human cells and plant cells in tissue culture.

Following expression in a host cell maintained in a suitable medium, the receptors may be isolated from the medium, and purified by methods known in the art. If the receptors are not secreted into the culture medium, the host cells are lysed prior to isolation and purification.

Cells that Express Receptors for Use as Antigens

Other sources of receptors for preparing the antibodies of the invention are receptors bound to the surface of cells. The cells to which the receptors are bound may be cells that naturally express the receptor, such as stem cells, including those of endothelial, muscle, or neural origin. Alternatively, the cell to which the full length or truncated receptor is bound may be a cell into which the DNA encoding the receptor has been transfected, such as 3T3 cells.

Preferred sources of mammalian stem cells that express receptors for use as antigens to prepare antibodies include bone marrow, adult peripheral or umbilical cord blood, or blood vessels. The cells may be isolated from bone marrow, blood, or blood vessels in accordance with methods known in the art.

Preparation of Antibodies

The antibodies are preferably monoclonal. Monoclonal antibodies may be produced by methods known in the art. These methods include the immunological method described by Kohler and Milstein in Nature X, 495–497 (1975) and Campbell in "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985); as well as by the recombinant DNA method described by Huse et al in Science 246, 1275–1281 (1989).

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256, 495–497 (1975). See also Campbell, "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985). In order to be useful, a peptide fragment must contain sufficient amino acid residues to define the epitope of the molecule being detected.

If the fragment is too short to be immunogenic, it may be conjugated to a carrier molecule. Some suitable carrier molecules include keyhole limpet hemocyanin and bovine serum albumen. Conjugation may be carried out by methods known in the art. One such method is to combine a cysteine residue of the fragment with a cysteine residue on the carrier molecule.

Some examples of antibodies that can be used to isolate endothelial, muscle, and neural stem cells that express high levels of human FLK-1 include the 6.64 or 4.13 antibodies, which are described in more detail below in example 1. Other antibodies useful in the invention are commercially available. For example, antibodies against the CD34 marker are available from Biodesign of Kennebunk, Me.

The molecule may also be a fragment of an antibody. The fragment may be produced by cleaving a whole antibody, or by expressing DNA that encodes the fragment. Fragments of antibodies may be prepared by methods described by Lamoyi et al in the Journal of Immunological Methods 56, 235–243 (1983) and by Parham in the Journal of Immunology 131, 2895–2902 (1983).

Fragments of antibodies useful in the invention have the same binding characteristics as, or that have binding characteristics comparable to, those of the whole antibody. Such fragments may contain one or both Fab fragments or the $F(ab')_2$ fragment.

Preferably the antibody fragments contain all six complementarity determining regions of the whole antibody, although fragments containing fewer than all of such regions, such as three, four or five CDRs, may also be functional.

The molecule is preferably labeled with a group that facilitates identification and/or separation of complexes containing the molecule.

Labelling of Probes

The molecules that bind to antigens that are characteristic of stem cells, as described above, may be labelled in order to facilitate the identification and isolation of the endothelial, muscle and neural stem cells. The label may be added to the molecule in accordance with methods known in the art. The label may be a radioactive atom, an enzyme, or a chromophoric moiety.

Methods for labelling antibodies have been described, for example, by Hunter and Greenwood in Nature 144, 945 (1962) and by David et al. in Biochemistry 13, 1014–1021 (1974). Additional methods for labelling antibodies have been described in U.S. Pat. Nos. 3,940,475 and 3,645,090. Methods for labelling oligonucleotide probes have been described, for example, by Leary et al., Proc. Natl. Acad. Sci. USA (1983) 80:4045; Renz and Kurz, Nucl. Acids Res. (1984) 12:3435; Richardson and Gumport, Nucl. Acids Res. (1983) 11:6167; Smith et al., Nucl. Acids Res. (1985) 13:2399; and Meinkoth and Wahl, Anal. Biochem. (1984) 138:267.

The label may be radioactive. Some examples of useful radioactive labels include $^{32}P$, $^{125}I$, $^{131}I$, and $^3H$. Use of radioactive labels have been described in U.K. 2,034,323, U.S. Pat. No. 4,358,535, and U.S. Pat. No. 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman, Proc. Natl. Acad. Sci., 47, 1981–1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules may be conjugated to the antibodies or nucleotides by means of coupling agents, such as dialdehydes, carbodiimides, dimaleimides, and the like.

The label may also be conjugated to the probe by means of a ligand attached to the probe by a method described above and a receptor for that ligand attached to the label. Any of the known ligand-receptor combinations is suitable. Some suitable ligand-receptor pairs include, for example, biotin-avidin or biotin-streptavadin, and antibody-antigen. The biotin-avidin combination is preferred.

EXAMPLES

Example 1

Monoclonal Antibodies 6.64 and 4.13.

The antigen used to generate the anti-KDR monoclonal antibodies 6.64 and 4.13 was a recombinately produced soluble form of the extra-cellular portion of the human KDR receptor. The cDNA encoding the extra-cellular domain of KDR was isolated by RT-PCR from human fetal kidney mRNA (Clontech, Palo Alto, Calif.). The DNA that encodes only the extracellular domain was subcloned into the Bgl II and BspE I sites of the vector AP-Tag (Flanagan and Leder, Cell 51, 185–194 (1990)). In this plasmid the cDNA for KDR extra-cellular domain was fused in-frame with the cDNA for human placental alkaline phosphatase (AP). The plasmid was electroporated into CHO cells together with the neomycin expression vector pSV-Neo and stable cell clones were selected with G418. The soluble fusion protein KDR:AP was purified from CHO cell culture supernatant by affinity chromatography using an immobilized monoclonal antibody to AP (anti-AP mouse monoclonal antibody #M10805, Medix Biotech, Inc., Foster City, Calif.) coupled to CnBr-activated Sepharose according to the manufacturer's instructions (Pharmacia Biotech Inc., Piscataway, N.J.). CHO cell conditioned media was passed over an anti-AP Sepharose column equilibrated in 50 mM Tris-HCl, pH 8.3, 0.5 M NaCl (equilibration buffer). The column was washed with 10 column volumes of equilibration buffer and then eluted with 10 column volumes of 0.2 M glycine-HCl, pH 3.2, 0.2 M NaCl. Fractions containing purified KDR:AP were pooled and concentrated. Purity of KDR:AP was >98% as determined by SDS-PAGE and N-terminal sequence analysis.

Female BALB/C mice, 8–12 weeks old, (Charles River) were injected sub-cutaneously in the posterior peritoneal area above the femoral lymph nodes on both sides of the mouse with 100 μg of KDR:AP/mouse in 0.2 ml/injection site of an emulsion prepared with the adjuvant Titermax (μCytRx Corp., Norcross, Ga.). After two weeks the mice were boosted with 100 μg of KDR:AP injected intraperitoneally. The boost was repeated two weeks later. One week after the last boost a test bleed was done and the mouse titer for anti-KDR antibodies was determined (see below for screening assays employed). In instances where the titer was low the boost injections and test bleeds were repeated. In situations where the titer was high the mice were rested and three to four days prior to fusion a final interperitoneal boost with 25 μg of KDR:AP was given.

Splenocytes were harvested from the mouse spleen and fused to mouse myeloma cells P3-X63/Ag8.653 (NS0/1) (ATCC, Rockville, Md.) using standard protocols (Harlow and Lane, Antibodies: A Laboratory Manual, Cold Spring Harbor Laboratory, Cold Spring Harbor, N.Y.) and seeded into 96-well plates in HAT medium supplemented with conditioned medium from the mouse macrophage cell line P388D$_1$ (ATCC, Rockville, Md.). The plates were scanned daily for signs of colony growth. On Day 5, the plates were fed 100 μl of HAT medium. On Day 12, samples of 200 μl/well were removed for testing and fed fresh HAT medium.

A high-throughput ELISA based primary monoclonal hybridoma screen was established which involved two assays run simultaneously. The assays were direct binding assays, one to the recombinant antigen KDR:AP and the second to AP alone (human placental alkaline phosphatase, cat. # p1391, Sigma, St. Louis, Mo.), both of which were directly immobilized to 96-well microtiter plates. The hybridoma supernatants were added to the plates, incubated for 1 h, washed and detected utilizing rabbit anti-mouse antibody-HRP conjugate. Antibodies specific for KDR were determined to be those positive on the KDR:AP plate but not on the AP-alone plate. Positive hybridomas were subsequently sub-cloned a minimum of three times. Subtyping was performed using the Isostrip kit (Boehringer-Mannheim Corp., Indianapolis, Ind.).

Purified anti-4 R monoclonal antibodies were produced by growing hybridomas in culture medium (RPMI 1640, 10% FCS, 2 mM L-glutamine) until cell density reached 5×10$^6$ cell/ml. Culture medium was then changed to HyMEM serum-free media (Hyclone, Logan, Utah) and cultures were maintained until viability reached <75%. Medium was then harvested by sequential filtration through a 5 um and 0.2 um membrane. Purification of the monoclonal antibody was accomplished by affinity chromatography on a Protein G-Sepharose FF column (Pharmacia Biotech Inc., Piscataway, N.J.). The conditioned hybridoma medium was adjusted to pH 8.5 and passed through a 10 ml Protein G column equilibrated in 50 mM Tris-HCl, pH 8.5, 0.5 M NaCl (buffer A). The column was washed with 10 column volumes of buffer A and the monoclonal antibody was eluted with 0.2 M glycine-HCl, pH 3.0, 0.5 M NaCl. Fractions containing the purified monoclonal antibody were pooled and concentrated.

Example 2

Isolation of CD34+ KDR+ Cells by Monoclonal Antibodies to KDR

Mononuclear cells from human bone marrow, peripheral blood or cytokine mobilized peripheral blood were depleted of red blood cells and platelets. Subsequently, the mononuclear hematopoietic cells were labeled with FITC-conjugated monoclonal antibody to KDR (clone 6.64, 4.13). FITC is fluorescein isothiocyanate, which in flow cytometry has green fluorescence. The flow cytometer can detect the green fluorescence emanating from FITC-KDR labeled cells. These cells were also incubated with Phycoerythrin conjugated-Monoclonal antibody to CD34. After removing the unbound antibody, the cells with bound CD34 and KDR were analyzed with two color flow cytometry. The cells that are labeled with both CD34 or KDR or other stem specific antigens such as AC133 can be used for automatic cell sorting by flow cytometry.

Deposit or Hybridomis

On Jan. 22, 1998, Applicants deposited with the American Type Culture Collection, Rockville, Md., USA (ATCC) the hybridoma cell lines that express the anti-KDR monoclonal antibodies listed below:

| NAME | Accession No. |
| --- | --- |
| Mab 6.64 | 12462 |
| Mab 4.13 | 12463 |

These deposits were made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

What is claimed is:

1. An isolated or purified population of mammalian endothelial stem cells comprising two endothelial stem cell markers on the surface of the endothelial stem cells, wherein one of the endothelial stem cell markers is a vascular endothelial growth factor (VEGF) receptor and the other endothelial stem cell marker is selected from the group consisting of AC133 and CD34, and wherein the purified population of mammalian endothelial stem cells is substantially fine of cells that do not express the two endothelial stem cell markers.

2. The isolated or purified population of mammalian endothelial stem cells according to claim 1 wherein the endothelial stem cells are derived from postnatal mammals.

3. The isolated or purified population of mammalian endothelial stem cells according to claim 1 wherein the endothelial stem cells are human endothelial stem cells.

4. The isolated or purified population of mammalian endothelial stem cells according to claim 1 wherein the VEGF receptors are KDR/FLK-1 receptors.

5. The isolated or purified population of mammalian endothelial stem cells according to claim 1 wherein the cells are KDR/FLK-1+CD34+AC133+.

6. The isolated or purified population of mammalian endothelial stem cells according to claim 1 wherein the cells are Lin$^-$.

7. The isolated or purified population of mammalian endothelial stem cells according to claim 1 wherein the VEGF receptors are present in an amount of at least 1,000 per cell.

8. The isolated or purified population of mammalian (endothelial stem cells according to claim 1 wherein the purified population of mammalian endothelial stem cells that express VEGF receptors constitutes 15–100% of the total population.

9. The isolated or purified population of mammalian endothelial stem cells according to claim 5 wherein the purified population of mammalian endothelial stem cells that express VEGF receptors and CD34 constitutes 15–100% of the total population.

10. The isolated or purified population of mammalian endothelial stem cells according to claim 2 wherein the post-natal source is circulating peripheral blood.

11. The isolated or purified population of mammalian endothelial stem cells according to claim 2 wherein the post-natal source is mobilized circulating peripheral blood.

12. The isolated or purified population of mammalian endothelial stem cells according to claim 2 wherein the post-natal source is umbilical cord blood.

13. The isolated or purified population of mammalian endothelial stem cells according to claim 2 wherein the post-natal source is bone marrow.

* * * * *